US00RE34851E

United States Patent [19]

Manning et al.

[11] E Patent Number: Re. 34,851

[45] Reissued Date of Patent: Feb. 7, 1995

[54] BIOSYNTHESIS OF 2 KETO-L-GULONIC ACID

[75] Inventors: Ronald F. Manning, Livingston, N.J.; Maria S. Kahn, Seattle, Wash.

[73] Assignee: Hoffmann-La Roche Inc., Nutley, N.J.

[21] Appl. No.: 950,523

[22] Filed: Sep. 25, 1992

Related U.S. Patent Documents

Reissue of:

[64] Patent No.: 5,082,785
Issued: Jan. 21, 1992
Appl. No.: 8,993
Filed: Jan. 30, 1987

[51] Int. Cl.[6] ..... C12N 1/21; C12N 15/00; C12P 7/60; C12P 7/58

[52] U.S. Cl. ..... 435/252.32; 435/252.3; 435/138; 435/172.3; 435/320.1; 435/137; 435/136; 536/23.1; 536/23.2; 536/24.1; 935/72; 935/29; 935/56

[58] Field of Search ..... 435/172.3, 320.1, 252.32, 435/252.3, 136, 137, 138, 183, 189, 190, 191, 91, 69.1; 985/6, 11, 14, 22, 29, 59, 60, 64, 72; 530/350; 536/27, 23.1, 23.2, 24.1

[56] References Cited

U.S. PATENT DOCUMENTS

| | | | |
|---|---|---|---|
| 3,907,639 | 9/1975 | Makover et al. | 435/138 |
| 4,468,464 | 8/1984 | Cohen et al. | 435/320.1 |
| 4,680,264 | 7/1987 | Puhler et al. | 435/172.3 |

FOREIGN PATENT DOCUMENTS 0132308 6/2594 European Pat. Off. .

OTHER PUBLICATIONS

Windholz et al. (eds.) 1983. The Merck Index., Merck & Co. Inc. Rahway, N.J. p. 445.

Berg et al. 1983 Bio/Technol. 1, 417–435.

Makover et al. 1975. Biotechnol. Bioengr. 17, 1485–1514.

Kuner et al 1981. Proc. Natl. Acad. Sci. USA 78, 425–429.

Nagahari et al 1978. J. Bacteriol. 133, 1527–1529.

*Primary Examiner*—Christopher S. F. Low

*Attorney, Agent, or Firm*—George M. Gould; William H. Epstein; Bruce A. Pokras

[57] ABSTRACT

A process of producing 2-keto-L-gulonic acid from sorbose via a recombinant bacteria including expression vectors and probes for producing said recombinant bacteria.

5 Claims, 6 Drawing Sheets

Model for Transposon Mutagenesis

RSF 1010: BROAD HOST RANGE PLASMID

BIOSYNTHESIS OF 2 KETO-L-GULONIC ACID

Matter enclosed in heavy brackets [ ] appears in the original patent but forms no part of this reissue specification; matter printed in italics indicates the additions made by reissue.

BACKGROUND OF THE INVENTION

The compound 2-keto-L-gulonic acid (2 KGA) is an important intermediate in the synthesis of ascorbic acid (Vitamin C). Numerous microorganisms are known to produce 2-keto-L-gulonic acid (2-KGA) from sorbitol or L-sorbose, for example, members of the genera Acetobacter and pseudomonas, (Japan Patent 40,154/1976). Numerous compounds have been proposed as intermediates in the production of 2-KGA from L-sorbose (Okazaki, et al. 1969. Agr. Biol. Chem. 33:207–211) the examples of this patent are concerned with the pathway through the intermediate L-sorbosone, and including the branch pathway to and from L-idonic acid; however, the principles involved in the invention apply to any pathway from L-sorbose to 2KGA. (Makover, et al. 1975, Biotechnol and Bioeng. 17:1485–1514.

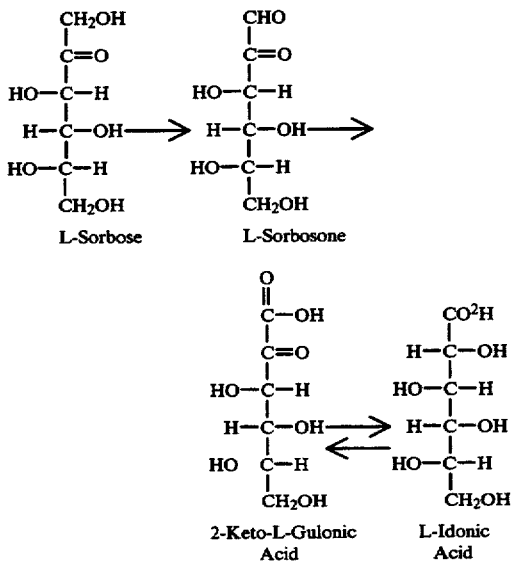

The microbiological conversion of L-sorbose to L-sorbosone is carried out by the enzyme L-sorbose dehydrogenase which is produced by the microorganism used. In a microbiological process for producing 2-KGA, the conversion of L-sorbosone to 2-KGA is carried out by the enzyme L-sorbosone dehydrogenase produced by the microorganism (U.S. Pat. No. 3,907,639). Many microorganisms which produce L-sorbosone dehydrogenase do not produce the enzyme L-sorbose dehydrogenase.

In some microorganisms the yield of 2-KGA can be lowered because of the activity of 2-KGA reductase, an enzyme which reduces 2-KGA to L-idonic acid. Other pathways exist for the metabolism of L-sorbose by various enzymes. Thus pathways lower the yield of 2-KGA. It is desirable to eliminate, or minimize these pathways by eliminating, or minimizing the production of competing enzymes and thereby enhance the yield of 2-KGA. Since 2-KGA is not essential for bacterial growth, it is not possible to select directly for efficient producers. Currently known microbial producers of 2-KGA have been obtained by screening very large numbers of natural isolates. Guanglin, et al. 1980. Acta Microbiologica Sinica 20: 246–251. It is desirable to provide simplified methods for improving the production of 2-KGA.

SUMMARY OF THE INVENTION

In accordance with this invention, transposon mutagenesis has been utilized to provide a method for producing 2KGA microbiologically as well as improving the production of microorganisms capable of producing 2-keto-L-gulonic acid from L-sorbose. By use of transposon mutagenesis in accordance with this invention the screening of transposon mutants is greatly simplified when compared to the screening of conventional mutants. Moreover, a transposon insertion provides a method for isolating and cloning a gene of interest entirely on the basis of its function. Such a gene can be manipulated so as to influence the production of 2-KGA from another organism. Hence, it is possible to improve the production of 2-KGA more easily than by conventional methods.

In accordance with this invention, improved methods are provided for the mutagenesis and the screening of organisms for the ability to produce 2-KGA. Therefore, through this invention, a new and improved process is provided for converting L-sorbose to 2-KGA microbiologically.

In accordance with this invention, a method is disclosed for identifying genes involved in the production of 2-KGA from L-sorbose.

In accordance with this invention, a method is disclosed for identifying genes involved in the production of 2-KGA from L-sorbose.

In accordance with this invention, a method is disclosed for constructing recombinant plasmids using the broad host range vector RSF1010. A method is also disclosed for introducing these plasmids into Gluconobacter oxydans or other bacteria.

These methods are used to identify and clone DNA coding for products involved in the production of L-sorbose dehydrogenase. When recombinant plasmids containing the L-sorbose dehydrogenase related DNA are transferred to a Gluconobacter oxydans which do not produce 2-KGA, these organisms obtain the ability to produce 2-KGA the same level as the organism which provided the L-sorbose dehydrogenase related DNA. Therefore, this invention provides an improved 25 method for producing 2-KGA.

FIGURE LEGENDS

DETAILED DESCRIPTION

Nucleotide—A monomeric unit of DNA consisting of a sugar moiety (pentose), a phosphate, and either a purine or pyrimidine base (nitrogenous heterocyclic). The base is linked to the sugar moiety via the glycosidic carbon (1' carbon of the pentose). That combination of a base and a sugar is called a nucleotide. Each nucleotide is characterized by its base. The four DNA bases are adenine ("A"), guanine ("G"), cytosine ("C") and thymine ("T").

DNA Sequence—A linear array of nucleotides connected one to the other by phosphodiester bonds between the 3' and 5' carbons of adjacent pentoses.

Genome—The entire DNA of a cell or a virus. It includes inter alia the structural genes coding for the polypeptides of the substance, as well as operator, promoter and ribosome binding and interaction sequences, including sequences such as the Shine-Dalgarno sequences.

Structural Gene—A DNA sequence which encodes through 35 its template or messenger RNA ("mRNA") a sequence of amino acids characteristic of a specific polypeptide.

Transcription—The process of producing mRNA from a structural gene.

Translation—The process of producing a polypeptide from mRNA.

Expression—The process undergone by a structural gene to produce a polypeptide, it is a combination of transcription and translation.

Plasmid—A circular double-stranded DNA Molecule that is not a part of the main chromosome of an organism containing genes that convey resistance to specific antibiotics. When the plasmid is placed within a unicellular organism, the characteristics of that organism may be changed or transformed as a result for the DNA of the plasmid. For example, a plasmid carrying the gene for tetracycline resistance (Tet®) transforms a cell previously sensitive to tetracycline into one which is resistant to it. A cell transformed by a plasmid is called a "transformant."

Cloning Vehicle—A plasmid, phage DNA or other DNA sequences which are able to replicate in a host cell, which are characterized by one or a small number of endonuclease recognition sites at which such DNA sequences may be cut in a determinable fashion without attendant loss of an essential biological function of the DNA, e.g., replication, production of coat proteins or loss of promoter or binding sites, and which contain a marker suitable for use in the identification of transformed cells, e.g., tetracycline resistance or ampicillin resistance. A cloning vehicle is often called a vector.

Cloning—The process of obtaining a population of organisms or DNA sequences derived from one such organism or sequence by asexual reproduction.

Recombinant DNA Molecule or Hybrid DNA—A molecule consisting of segments of DNA from different genomes which have been joined end-to-end outside of living cells and have the capacity to infect some host cell and be maintained therein.

Figure 1:
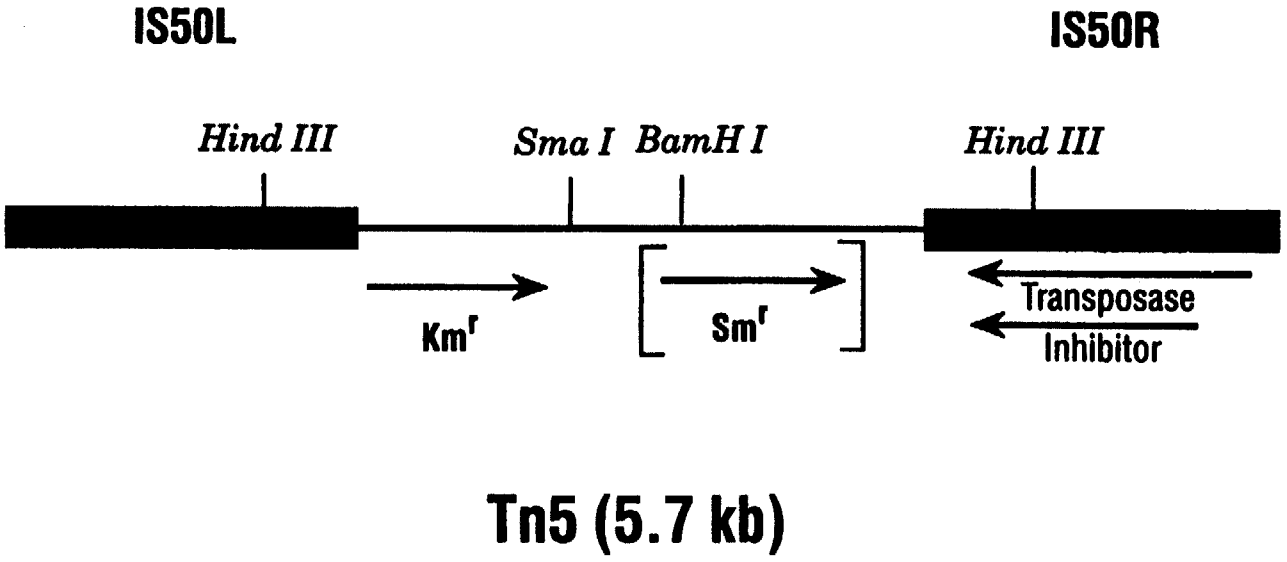
FIG. 1 is a restriction endonuclease site map of Tn5 based on Berg, D and Berg, C, Biotechnology 1:417–435 (C1983).

Transposons are a class of movable genetic elements which can not replicate independently, but must insert themselves into a host DNA in order to be propagated (Kleckner, N., Roth; and Botstein, D. 1977. J. Mol. Biol. 116:125–159. This host DNA insertion can occur at one of many sites (Shan, K. and Berg, C. 1979, Genetics 92:741–747. The distribution of transposon Tn5 insertion sites in many bacterial DNA's appears to be more random than that of any other transposon studied. Other transposons can be used for this purpose, Tn5 is preferred (FIG. 1).

Figure 2:
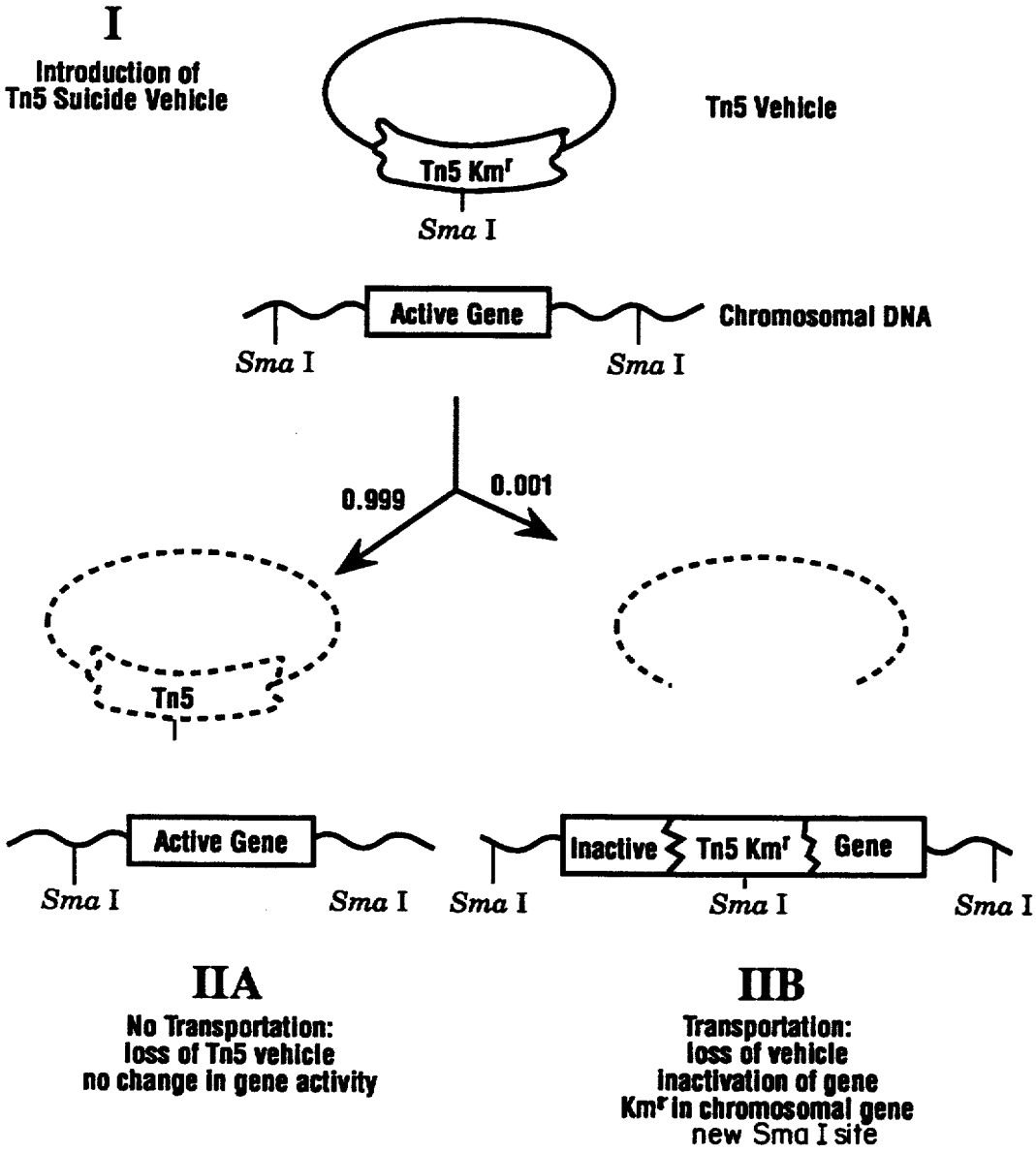
FIG. 2 illustrates transposon mutagenesis with regard to Tn5.

When Tn5 is inserted within a functional gene, as seen from FIG. 2, the activity of that gene will be lost and a transposon mutant will be created.

Transposon Tn5 codes for activities which regulate its own transposition (Berg, D. and Berg C, 1983, Biotechnology 1:417–435). In addition, Tn5 contains antibiotic resistance markers for kanamycin and streptomycin. Hence, selective procedures can be used in transposon manipulation.

Transposon mutagenesis is well suited for improving the production of non-essential microbiological products such as 2-KGA. The transposition of a transposon in a cell is self limiting, hence, a cell rarely has more than one copy of a given transposon. Hence, screening of transposon mutagenized cells is simplified. One can utilize the transposon borne antibiotic-resistance marker to assure that only mutagenized cells are screened. The self limiting aspect of transposon insertion assures that only single—mutants are screened. A transposon mutation also places a very useful label on an otherwise "non-selectable gene". Thus marked, the mutant gene can be isolated, so that its wild type counterpart can be cloned.

In accordance with this invention, the 5.7 kb Tn5 (FIG. 1), which codes for kanamycin resistance (Km') in E. coli but determines streptomycin resistance (Sm') as well in many gram negative soil bacteria can be utilized for constructing a probe for L-sorbose dehydrogenase related DNA.

Figure 3:
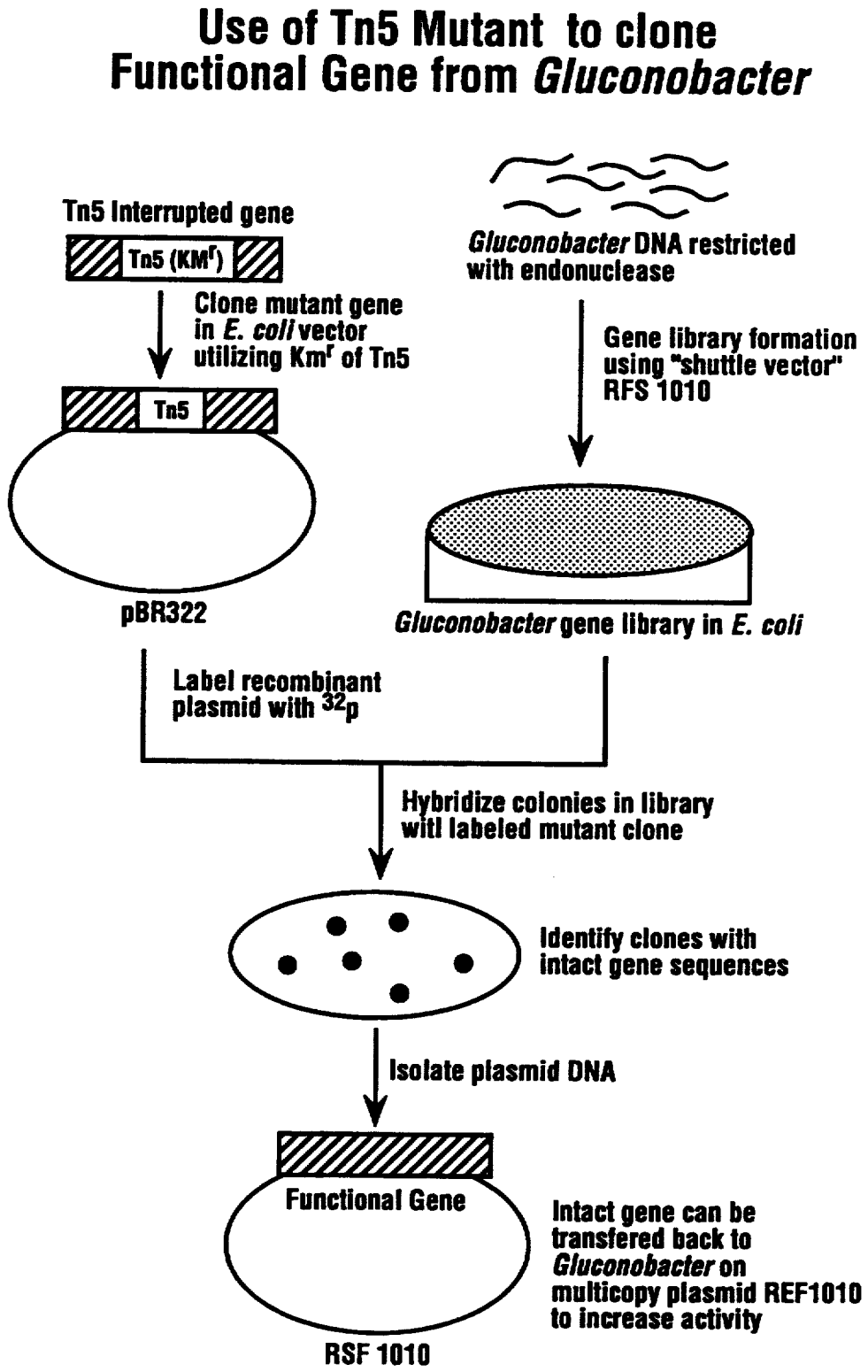
FIG. 3 illustrates the structure of both the probe for the gene capable of expressing L-sorbose dehydrogenase and the construction of the plasmid containing this gene.

The overall process of Tn5 mutagenesis is outlined in FIG. 3. In this procedure, Tn5 is introduced on a "suicide" delivery vehicle which cannot be maintained in the target cell. Suitable vehicles are R91-5 and pSup2021, the preferred vehicle being pharge pl (Kuner and Kaiser. 1981 PNAS U.S.A. 78:425–429). In most recipient cells, the vehicle and the Tn5 are lost from the cell at the same time. However, on occasion, the Tn5 will move to a site in the host cell DNA before the vehicle is lost. This new site as well as the entire cell, now has the Km' market of the Tn5. If the site is within a functional DNA sequence, the activity of that sequence will be lost. In accordance with a preferred embodiment of this invention, transposon mutagenesis can be carried out on a G. oxydans strain which can produce about 20 g/l 2-KGA from 70 g/l L-sorbose. The identification of the 2-KGA producing organism as a Gluconobacter oxydans is based on the description as given in "Bergey's Manual of Systematic Bacteriology", Vol. 1, pp. 275–278, 1984. Strain UV10 is a suitable host for this purpose. However, any strain which produces 2-KGA from L-sorbose can be utilized for the purposes of this invention.

In order to identify cells which are mutagenized in the L-sorbose to 2-KGA pathway, kanamycin resistant (Km') cells are grown at 30° C. in a suitable medium containing 7% by weight L-sorbose and a suitable nitrogen source. After 5 days, the fermentation products are screened for 2-KGA, and other sorbose metabolites by methods familiar to those practiced in the art.

Some Gluconobacter pathways which utilize L-sorbose or a derivative thereof, compete with the production of 2-KGA. One such pathway is the reduction of 2-KGA to L-idonic acid (Ameyama, M. and Adachi, O. 1982. Methods in Enzymology 89:203–211)(Makover et al. 1975, supra). A Tn5 mutant which has lost this competing pathway can be expected to produce more 2-KGA.

Therefore, through transposon mutagenesis one can improve the ability of a microorganism to produce 2-KGA from L-sorbose by creating a mutant of this microorganism in which one or more of the competing side reactions are blocked. This is accomplished by inactivating the DNA capable of expressing an enzyme which causes side reactions by the insertion of a transposon therein. These enzymes, cause side reactions to produce sugars other than 2-KGA which decrease the yield of 2-KGA. One such enzyme is 2-keto-L-gulonic acid reductase which reduces 2-KGA to L-idonic acid. By conventional screening of the mutants produced by transposon mutagenesis for lower L-idonic acid production, one can obtain mutants of the original sorbose to 2-KGA producing strain which has improved 2-KGA production due to the insertion of the transposon in the DNA encoding for the enzyme 2-keto-L-gulonic acid reductase. Though conventional mutants are capable of inactivating the 2-KGA reductase gene, screening for such blocked mutants is simpler for Tn5 mutants because only mutants are isolated and screened, due to their Km' character. Such mutants are virtually always single mutants.

Certain other Tn5 mutants can lose the activity of enzymes directly connected with the production of 2-KGA, some such mutants can lose the ability to produce L-sorbose dehydrogenase. Such mutants are considered to have Tn5 inserted into a DNA which is required for the synthesis of L-sorbose dehydrogenase. This L-sorbose dehydrogenase related DNA may be a structural gene or a regulatory element whose function is essential for the synthesis of L-sorbose dehydrogenase. The chromosome of the Tn5 mutant lacking the activity of L-sorbose dehydrogenase, or any other activity required for 2-KGA production, will consist of DNA from a microorganism such as Gluconobacter which is interrupted at some point by DNA, of the transposon such as Tn5. This DNA can be isolated from the mutant cell. From the resulting isolated DNA the probe of this invention can be constructed. This probe is constructed by combining DNA containing the Tn5 interrupted L-sorbose dehydrogenase related DNA with a suitable vector. This recombinant plasmid can be cloned by insertion into a suitable host cell which will allow its reproduction.

A wide variety of host/cloning vehicle combinations may b e employed in cloning the double-stranded DNA. For example, useful cloning vehicles may consist of segments of chromosomal, non-chromosomal and synthetic DNA sequences, such as various known bacterial plasmids, e.g., plasmids from E. coli such as PBR322, phage DNA and vectors derived from a combination of plasmids and phage DNA's such as plasmids which have been modified to employ phage DNA or other expression control sequences or yeast plasmids. Useful hosts may include microorganisms, mammalian cells, plant cells and the like. Among them, microorganisms and mammalian cells are preferably employed. As preferable microorganism, there may be mentioned bacteria such as Escherichia coli, Bacillus subtilis, Bacillus stearothermophilus and Actinomyces. Of course, not all host/vector combinations may be equally efficient for cloning. This particular selection of a host/-cloning vehicle combination may be made after due considerations of the principle set forth without departing from the scope of this invention.

Furthermore, within each specific cloning vehicle, various sites may be selected for inserting the doublestranded DNA. These sites are usually designated by the restriction endonuclease which cuts them. For example, in PBR322 the ClaL site may be utilized for inserting the DNA sequence interrupted with Tn5. Various sites have been employed by others in the synthesis of recombinant plasmids. Several sites are well recognized by those skilled in the art. It is, of course, to be understood that a cloning vehicle useful in this invention need not have a restriction endonuclease site for insertion of the chosen DNA fragment. Instead, the vehicle could be joined to the fragment by alternate means.

There are several known methods of inserting DNA sequences into cloning vehicles to form recombinant DNA molecule which could be useful in this invention. These include, for example, direct ligation, synthetic linkers or the formation of complementary overlapping fragments by the use of terminal transferase to extend 3'OH termini, followed by annealing of the overlapping fragments to form a recombinant plasmid.

As seen from FIG. 3, the insertion of the DNA required for L-sorbose dehydrogenase interrupted by Tn5 in a vector into a host cell can be carried out by conventional means. Among the preferred host cells especially where the vector is a PBR322, is included E. coli. The transformed host thereby clones this recombinant plasmid. To form a probe, as illustrated in FIG. 3, one extracts the plasmid and radiolabels the DNA by conventional techniques.

The probe prepared above can be utilized in accordance with this invention to screen various DNA fragments to determine if they have the unmutated DNA sequence required for expressing L-sorbose dehydrogenase.

In forming a DNA library of FIG. 3 for later screening to determine the presence of genes capable of inducting the expression of one or more of the enzymes utilized in the conversion of L-sorbose to 2KGA, the DNA is removed from any organism which is capable of converting sorbose to 2KGA preferably Gluconobacter oxydans UV10. This DNA is restricted by endonucleases which recognize a four base sequence which is common in Gluconobacter oxydans. A preferred enzyme is Hhal which recognizes the sequence GCGC. The extent of restriction is limited by well known means so that most of the DNA fragments are between 5 and 10 kb in length, a preferred size for forming a library, though DNA of other lengths may be employed. DNA of the preferred length is isolated by well known means. The enzyme terminal transferase (TdT) is employed to add an oligonucleotide extension of dC. residues onto the 3'OH ends of the isolated Gluconobacter oxydans DNA. A preferred extension length is 15–20 bases.

Figure 4:
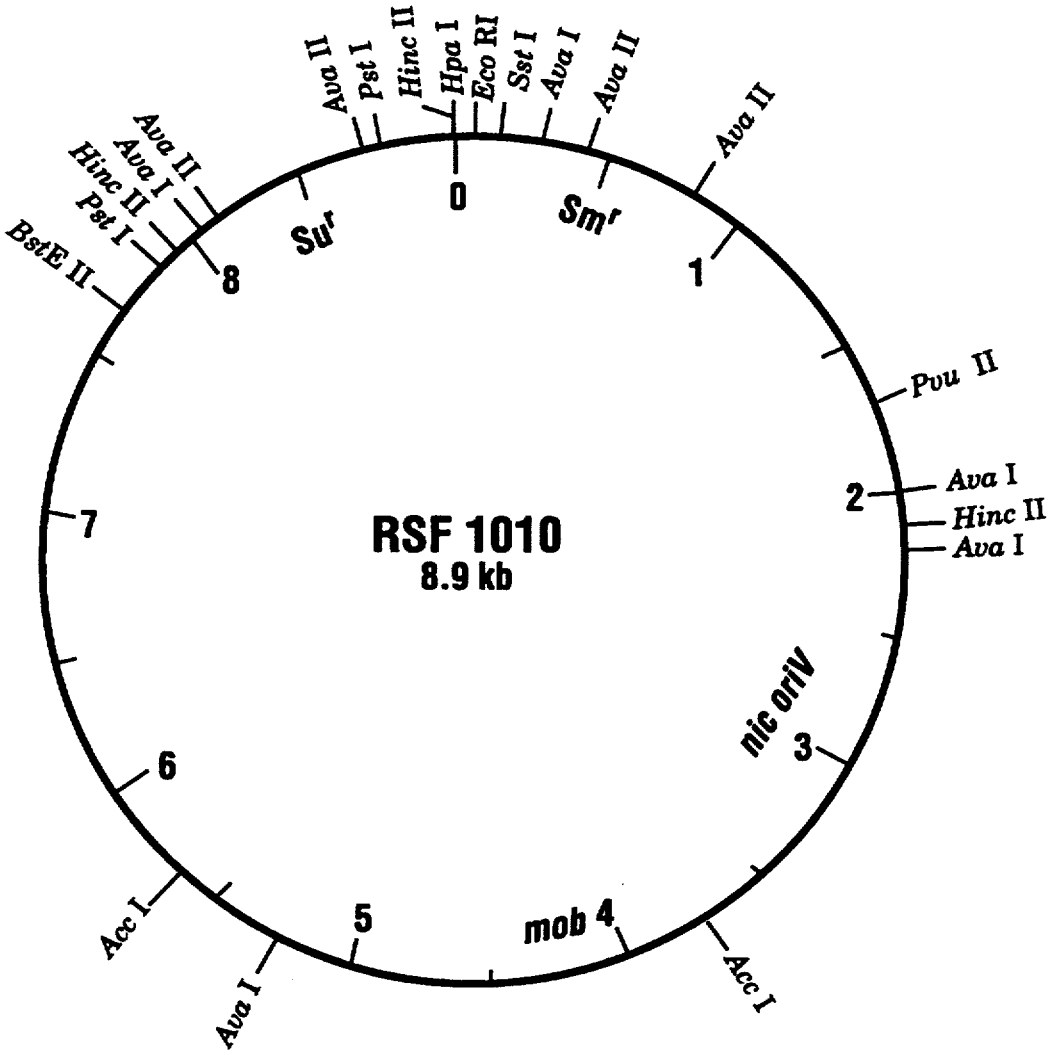
FIG. 4 is a restriction endonuclease site map of RSF1010.

The vector employed to form the library in FIG. 3 is one which can replicate in Gluconobacter, as well as a preferred cloning organism such as E. coli. The preferred vector is RSF1010 (Nagahari, K. and Sakaguchi, K. 1978. J. Bact. 133:1527–1529) (FIG. 4), but any vector which can replicate in Gluconobacter as well as E. coli can be employed. The RSF1010 vector is restricted with an endonuclease such as PvuII which recognizes a site, CAGCTG, that is not in a region of the plasmid required for replication or antibiotic resistance. Terminal transferase is employed to extend the 3'OH ends of the vector with dG residues to a preferred length of 15–20 bases.

The 3'OH extended vector and Gluconobacter DNA are annealed together to form recombinant molecules by well known means. The recombinant molecules are used to transfect a preferred host such as E. coli. A given wild type Gluconobacter sequence should be present at least once in a DNA library of 3000 such independent recombinants.

FIG. 3 illustrates the identification by means of the probe of the clones in the wild type gene library which contain this L-sorbose dehydrogenase related gene. In order to identify which recombinant clones in the library contain the wild type L-sorbose dehydrogenase related DNA, the clones are hybridized with the probe prepared from the Tn5 mutated DNA by well known means.

The recombinant plasmid containing the wild type L-sorbose dehydrogenase related DNA can be transferred to a recipient microorganism by transfection or mobilization, which is the preferred method (Okumura, et al. 1985, Agric Bio Chem. 49:1011–1017). The wild type L-sorbose dehydrogenase DNA inserted into a suitable vector such as RSF1010 can be mobilized to a suitable recipient by conjugal transfer of the plasmid from the E. coli host to the recipient if a suitable helper plasmid is present in the E. coli host or a third cell to provide plasmid transfer functions. The conjugation can occur in liquid medium or on a solid surface, which is preferred. The preferred recipient is an organism, such as IF03293 which possesses L-sorbosone dehydrogenase activity. The helper plasmid can be an independent replicon or integrated into the cell chromosome. A preferred helper plasmid is RP4, but others familiar to those well versed in the art can be employed.

Following transfer to the recipient, the recombinant plasmid may replicate as a free plasmid or portions of the plasmid may integrate into chromosomal or plasmid DNA of the cell.

The cloned L-sorbose dehydrogenase related DNA may function in the new host to complement a gene product which the host requires for L-sorbose dehydrogenase activity. This may be a structural protein with L-sorbose dehydrogenae activity, an accessory protein, or a regulatory element. A host cell with L-sorbosone dehydrogenase activity which obtains the cloned DNA required to synthesize L-sorbose dehydrogenase thus will be able to produce 2-KGA from L-sorbose.

Production of 2-KGA by the recipient may be determined by growth in a medium containing L-sorbose, followed by 2-KGA assay.

In the following examples, the following microorganisms were utilized.

| Strains | Deposit |
|---|---|
| *Gluconobacter oxydans melanogenus* UV10 | FERM-BP-1267 |
| G.O. Suboxydans TF03293 | FERM-P No. 8356 |
| *E. coli* W311') (P1::Tn5) | NRRL B-18148 |
| *E. coli* 600 | ATCC 33525 |
| *E. coli* C600 (RSF1010) | NRRL B-18146 |
| *E. coli* J53 (RP4) | NRRL B-18147 |
| *G. Oxidans* M25-18 | NRRL B-18143 |
| *G. Oxidans* M43-53 | NRRL B-18144 |
| *G. Oxidans* M23-15 | NRRL B-18145 |

In the above table, FERM designates that the strain is deposited with the Agency of Industrial Science and Technology. Fermentation Research Institute. Japan. The term NRRL designates the strain is deposited with the northern regional research center of United States Department of Agriculture peoria, Illinois.

EXAMPLE 1

Coliphage Pl: Tn5 and a protocol for its use were supplied by C. Berg, U. of Conn.

A starter culture of E. coli W3110 (pl:Tn5) is grown for 18 to 20 hours at 30° C. in LB medium (10 g/l NaCl, 10 g/l Bacto Tryptone, 5 g/l yeast extract) with continuous agitation. One ml of the culture is diluted into 100 ml pl medium (LB medium, 10 mM $MgCl_2$, 10 mg/ml thymidine) and grown at 30° C. to an $A_{550}$ (absorption at 550 nm in a 1 cm light path) of 0.092. The cells are chilled on ice 10 min., pelleted at 2,500 rpm 10 min. at 6° C. and resuspended in 20 ml pl medium. Phage production is induced at 42° C. for 20 minutes, then 37° C. for 90 minutes. Cell lysis is completed by the addition of 0.5 ml of chloroform, vortexing, and incubating at room temperature 5 min. Cell debris is pelleted at 10,000 rpm 15 min. The supernatant is diluted into a ten fold excess of MCB (10 mM $MgCl_2$, 10 mM $CaCl_2$) and used as the phage suspension.

The preferred recipient strain for pl:Tn5 is

Gluconobacter oxydans strain UV10, which produces 20–25 g/l 2KGA from 70 g/l L-sorbose. A culture of the recipient is grown in MMB broth (25 g/l mannitol 5 g/l yeast extract, 3 g/l bacto peptone) at 28° C. for 18–20 hours, then 1 ml is diluted into 29 ml MB broth and grown to $A_{550}=0.4$. The cells are pelleted at 2,500 rpm, 6° C., and suspended in 1.8 ml MCB. To infect, 0.1 ml of cells are mixed with 0.1 ml phase suspension and incubated at 30° C., 60 minutes.

The infected cells are then diluted with 0.8 ml MB broth and placed at room temperature for 2 hours, plated on MBA (MB, 15 g/l agar) containing 50 μg/ml kanamycin, and incubated at 30° C. 3–45 days. Cells which form colonies contain Tn5 inserted into the chromosome.

Mutant Analysis

Kanamycin resistant mutant colonies were grown in 5 ml seed medium (10 g/l $CaCO_3$, 7.5 g/l yeast extract, 70 g/l sorbitol, 0.5 g/l glycerol, 2.5 g/l $MgSO_4 \cdot 7H_2O$, 50 μg/ml Km) at 27° C., 48 hours, and 0.5 ml was transferred to 5 ml of 70 g/l sorbose, 0.05 g/l glycerol, 12 g/l $CaCO_3$, 2.5 g/l $MgSO_4$, 5 g/l yeast extract, 15 g/l corn step liquor, 50 μg/ml Km, and grown at 27° C., 5 days. Fermentation products was analyzed by high performance liquid chromatography (HPLC). Broth aliquots of 100 μl were mixed with 2 ml of 0.5% o-phenylene diamine dihydrochloride for 30 minutes at 90° C. in a sealed vial. Chromatography was performed on a C. 18 u bond pak (30 cm×3.9 mm i.e.); mobile phase, methanol/$H_2O$ (75:25); flow rate 2 ml/min; 2000 psi.

In addition, thin layer chromatography (TLC) was performed by spotting 1 μl of culture broth on a silica gel plate, and developing the plate with n-propyl alcohol, water, 1% phosphoric acid, and formic acid (100:25:2.5:0.25). Following development, the plates were sprayed with tetrazolium blue or tetrabase according to standard methods.

Following TLC analysis of 2000 UV10:Tn5 mutants, one mutant, M23-15, appeared to produce more 2-KGA than the parent culture. Thin layer chromatography of fermentation products also showed that the by product idonic acid was greatly reduced.

To confirm these findings, a loopful of the parent culture UV10, and the mutant M23-15 were grown overnight at 30° C. in 2 ml MB medium, 50 μg/ml km; 100 μl of the culture was transferred to 10 ml M3B medium (70 g/l L-sorbose, 10 g/l $CaCO_3$2.5 g/l $MgSO_4$·7. $H_2O$ 5 g/l yeast extract, 0.5 g/l glycerol) 50 μg/ml Km in a 50 ml flask, 30° C. for 5 days with vigorous aeration. Levels of 2KGA were quantitated by HPLC. To measure L-idonic acid, the pH of the sample was adjusted between 1.5 and 2.0, and it was heated to 80° C. for 1 hr., to produce idonolactone. One ml of the lactone solution was added to 2 ml of an equal volume solution of 4M hydroxylamine hydrochloride and 4M sodium hydroxide. Absorbance at 540 mm was measured against a similarly treated water blank. The concentration of L-idonio acid was determined by comparison with a standard curve and the results are given in Table I.

TABLE I

| Production of 2-KGA and Idonic Acid by Tn5 Mutant 23-15 | | |
|---|---|---|
| | 2-KGA | Idonic Acid |
| UV10 | 19.6 g/L | 10.9 g/L |
| M23-15 | 33.3 g/L | 2.8 g/L |

As seen in Table 1, the mutant M23-15 produces considerably more 2KGA than the parent, UV10, at the same time the output of the side product, L-idonic acid is reduced.

L-Idonic acid is produced by 2-KGA reductase, which reduces 2-KGA, utilizing NADPH as a cofactor. Accordingly, the 2-KGA reductase in M23-15 and the parent strain, UV10 was assayed.

A loopful of culture was grown to saturation in 5 ml MB medium. 1 day, 30° C., 300 rpm. Two ml of this culture were transferred to 100 ml MB medium in a 500 ml Erlenmeyer flask and grown 1 day, 30° C. 300 rpm. Twenty ml of this growth was used for inoculation of each of 2 flasks of M3B medium, 500 ml per 2000 ml flask, and grown for 3 days, 30° C. 300 rpm. The broth was centrifuged at 400 rpm for 10 min., 4° C., to remove the $CaCO_3$, then at 4000 rpm, 20 min., 4° C., to pellet the cells. The cell pellet was washed twice with ice cold, sterile 0.85% NaCl.

Three grams of cells were resuspended in 10 ml 10 mm $MKPO_4$, pH 7, and homogenized for 2 min. in a Biospec products Bead Beater. The homogenate was centrifuged at 8.800 xg. 4° C. 10 min. to remove cellular debris, and then at 100,000xg, 4° C., 60 min. The supernatant was used as the cytosol enzyme fraction. Units of enzyme activity in micromoles of product formed in 1 min. at 25° C. was measured by reading the change of absorbance of reduced pyridine cofactor at 340 nm in a reaction mixture of 1 mg 2-KGA (100 μl of a 10 mg/ml solution in 50 mM $KPO_4$, pH 7.0), 50 μl 2 mg/ml NADPH in 50 mM $KPO_4$(pH 7.0), 25 μl cytosol enzyme fraction and 625 μl 50 mM $KPO_4$(pH 7), protein concentration was measured using the Bio Rad protein Assay according to the manufacturer's instructions.

TABLE II

| Specific Activity of 2KGA Reductase U/mg Protein | |
|---|---|
| UV 10 | 0.0343 |

TABLE II-continued

| Specific Activity of 2KGA Reductase U/mg Protein | |
|---|---|
| M23-15 | 0.000067 |

Table II clearly shows that the 2-KGA reductase activity of M23-15 is much lower than that of UV10. Hence by this method one obtains a microorganism which produces 2-KGA more efficiently than the parent culture.

EXAMPLE 2

Cloning of Genes Involved in L-Sorbose Dehydrogenase Synthesis

Tn5 mutageneis of the 2KGA producing Gluconobacter. Oxydans UV10 and a subsequent analysis of 5000 mutants allowed the isolation of numerous strains which produced less 2-KGA than the parent. Four of these produced less than 1 g/l 2-KGA.

In these strains, the Tn5 has inactivated a DNA sequence which is essential for 2-KGA production. Two enzyme activities are involved in the production of 2KGA by strain UV10; L-sorbose dehydrogenase, which oxidizes L-sorbose to L-sorbosone, and L-sorbosone dehydrogenase, which further oxidizes L-sorbosone to 2-KGA. To distinguish which of these activities is lacking, seed cultures of mutant and wild type cells were grown in MB media at 30° C., 1 day; 2 ml of seed culture was used to inoculate 100 ml M3B, 50 μg/ml Km, in a 500 ml flask. After 2 days, 30° C., 25 ml of cell culture was chilled on ice, pelleted, washed twice with 40 mM ADA [N-(2-acetamido)-immodiacetic acid], pH6.8 at 4° C., then suspended in 20 mM ADA, ph6.8 containing either 7% L-sorbose or 2% L-sorbosone and incubated at 30° C., 2 days with vigorous aeration. Production of 2-KGA was assayed by HPLC, results are shown in Table III.

TABLE III

| Production of 2-KGA from L-Sorbose or L-Sorbosone by Non-Growing Cells | | |
|---|---|---|
| | 2-KGA (g/l) | |
| | L-Sorbose | L-Sorbosone |
| UV 10 | 8.3 | 6.1 |
| M2518 | 0 | 2.7 |
| M4353 | 0 | 3.8 |
| M4191 | 0 | 2.9 |

The wild type control cells could easily convert either L-sorbose or L-sorbosone to 2KGA, whereas the mutant types could only convert L-sorbosone to 2KGA. The mutant cells are not deficient in L-sorbosone dehydrogenase, suggesting a defect in L-sorbose dehydrogenase.

To confirm the defect in L-sorbose dehydrogenase activity, enzyme levels were determined. A loopful each of UV10, M43-53, M25-18 and M47-118 were used to inoculate 15 ml of mannitol broth medium. The stationary cultures (1 day) were used to inoculate 100 ml MB, grown 1 day, and then inoculated and grown in M3B as described in example 1. Cells were harvested and homogenized as following 100,000 xg centrifugation of the homogenate, the pelleted fraction was collected as the membrane fraction. The membrane fraction was suspended in 4 ml 10 mM $KPO_4$, pH 7 For solubilization, 0.6 ml of membrane sujspension was mixed with 2.4 ml 10 mM $KPO_4$, pH 7, containing 0.3%

Triton X-100, in a 50 ml blank buffer by stirring for 3 hrs, and was then centrifuged at 100,000 xg for 1 hr. The supernatant was designated the solubilized membrane fraction. The enzyme assay was performed by measuring the decrease in absorbance at 600 nm of 2,6-Dichlorophenolendophenol (DCIP). One unit of activity is defined as the amount of enzyme which catalyzes the reduction of 1 μ mole of DCI per minute at 25° C. The assay mixture contained 280 μl 0.1M $KPO_4$, pH 7.0, 0.3% Triton X-100, 40 μl of 2.5 mM DCIP; 200 μl of 1M L-Sorbose, and 10 μl enzyme solution, and 470 μl $H_2O$. protein concentrations were determined as in Example 1.

TABLE IV

| Specific Activity of Membrane Bound L-Sorbose Dehydrogenase U/mg Protein | |
|---|---|
| UV 10 | 0.194 |
| M25-18 | 0.023 |
| M43-53 | 0.013 |
| M47-118 | 0.007 |

The mutant cells clearly lack L-sorbose dehydrogenase activity, indicating that a Gluconobacter DNA sequence essential for the synthesis of L-sorbose dehydrogenase has been inactivated.

Cloning of Tn5-Mutant DNA

Total DNA was isolated from the mutant strains according to well known methods. The DNA was digested with various restriction enzymes fractionated by electrophoresis on 1% agarose and blotted to nitrocellulose filters, all according to standard procedures. (Maniatis, et al., Molecular Cloning, a Laboratory Manual, Cold Spring Harbor Laboratory press, Cold Spring Harbor, 1982). The blotted DNA was annealed to ColEl::Tn5 DNA which had been labeled with 32p by nick-translation and homologous fragments detected by autoradiography.

The lengths of the DNA fragments which annealed to the Tn5 probe were calculated, these values are shown in Table V.

TABLE V

| Restriction analysis of DNA from L-Sorbose Dehydrogenase Deficient Tn5 Mutants | | | |
|---|---|---|---|
| | Fragment Length | | (Sum of Lengths) |
| Mutant | Cla I | Eco RI | Bam HI |
| M25-18 | 16 Kb | 16.5 Kb | 5.0<br>8.2 (13.2) |
| M38-97 | 16 | 16.5 | 5.2<br>8.5 (13.7) |
| M41-91 | 9.2 | 27 | 7.6<br>8.5 (16.1) |
| M43-53 | 9.2 | 27 | 7.0<br>9.5 (16.5) |

Clearly, two different types of 2-KGA-mutants have been obtained, according to the location of the Tn5, M25-18 and M38-97 are in group 1; M43-53 and M41-91, comprise group 2.

The region of chromosomal DNA from M25-18 and M43-53 which were inactivated by Tn5 were cloned into E. coli using the vector PBR322 by the following procedure. DNA from the mutants were restricted with Cla I and electrophoresed on 0.7% agarose gels. The DNA of the correct size was cut out of the gel and eluted. About 200 ng of mutant DNA was obtained in each case. About 2 μg of PBR322 DNA was restricted at its unique Cla I site and treated with calf alkaline phosphatase according to standard methods. Mutant and vector DNA's were ligated with T4 DNA ligase, and the recombinant plasmids were used to transform E. coli strain C600. Since Tn5 contains the neomycin phosphotransferse, gene, recombinant cells were selected on the basis of Km'.

plasmids were obtained from the Km' transfectants by a rapid method of alkaline lysis (Birnboim and Doly 1979, Nuc. A. Research, 7:1513–1523.) The plasmids were restricted and electrophoresed in order to confirm that the correct fragment had been cloned. Clone PM25-18 contains the mutated group 1 L-sorbose dehydrogenase sequence: PM43-53, that of group 2.

In order to obtain the clone of the corresponding wild type DNA, a library of unmutated DNA from strain UV10 was prepared using the broad hos range vector RSF1010. About 200 μg of total DNA from UV10 was partially restricted with about 10 units of HhaI for 1 hr, fragments of 5–10 kb were obtained by gel electrophoresis and elution. Terminal transferase (TdT) was used to lengthen the 3' OH termini of the fragments with 15–20 deoxycytidine residues. About 5 μg of RSF1010 were linearized by restriction with PvuII. The 3'OH termini of vector was then extended by 15–20 deoxyguanidine residues. 100 ng each of the now complementary ends of the vector and insert were annealed at a 1:1 ratio for 3 hrs. at 65° C. in 100 μl of 150 mM NaCl, 10 mM Tris (pH 7.9) and 0.1 mM EDTA, and slowly cooled to room temperature; 20 μl was used to transfect E. coli C600.

Figure 5:
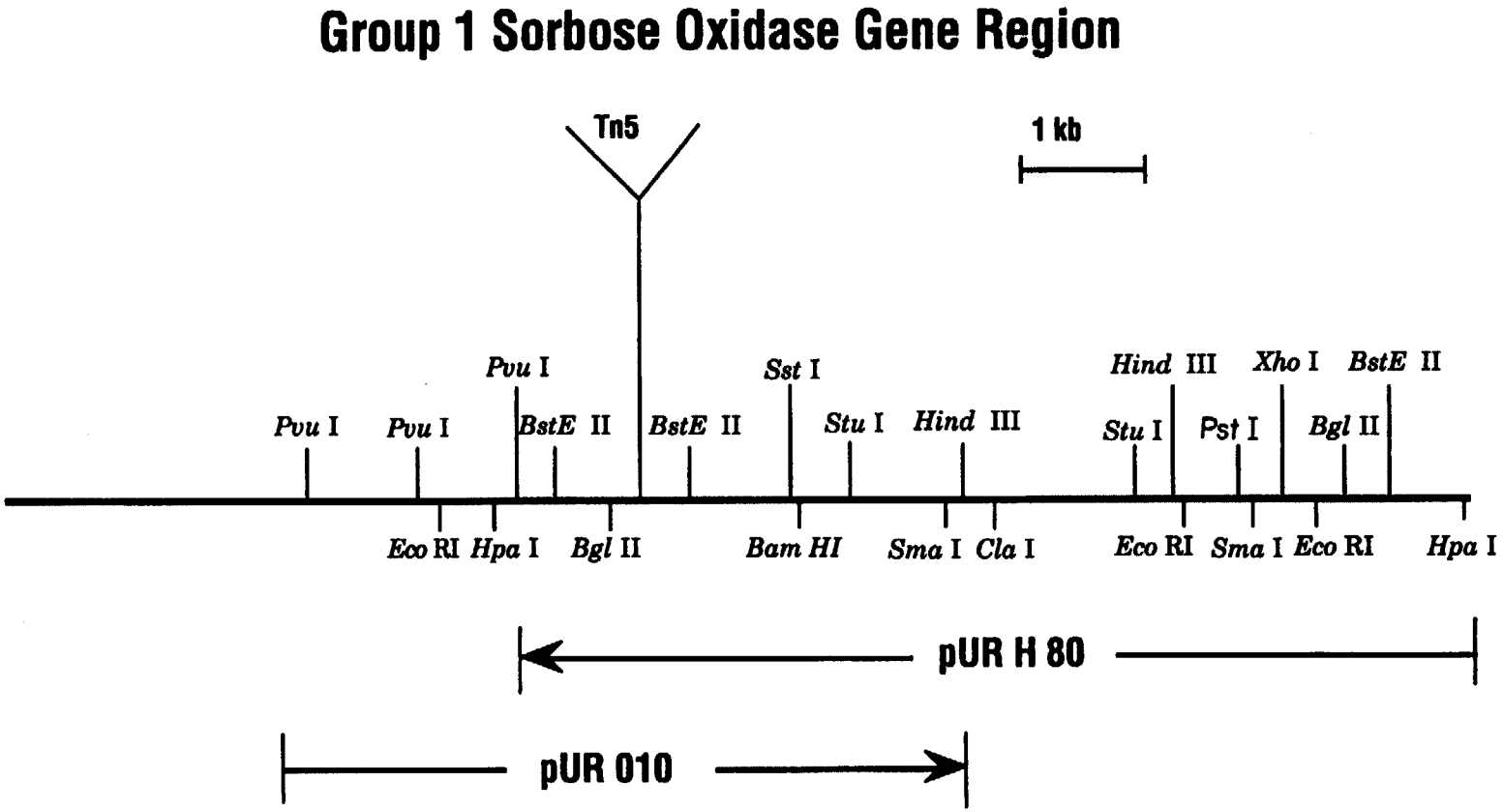
FIG. 5 is a restriction endonuclease site map of the Group I L-sorbose dehydrogenase (Sorbose oxidase) gene region.
Figure 6:
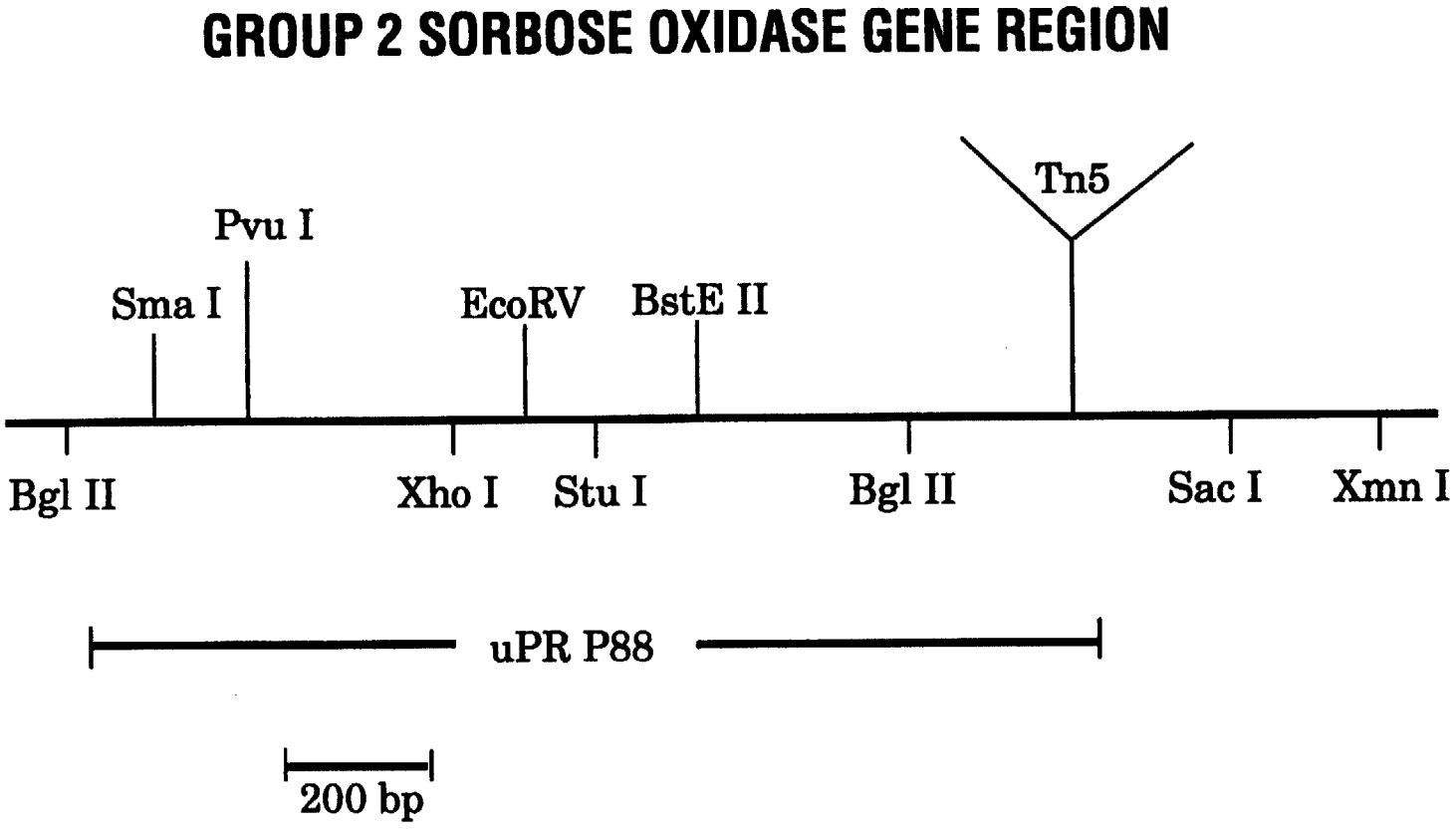
FIG. 6 is a restriction endonuclease site map of the Group 2 L-sorbose dehydrogenase (Sorbose oxidase) region.

About 3000 recombinant colonies were obtained following selection on LB agar containing streptomycin. The DNA from a replica of the colonies was transferred in situ to a set of nylon membrane filter and annealed first to 32p labeled PM25-18. Two different group 1 recombinants were obtained, PURUH80 and PURU010 (Fig. 5). The radiolabelled DNA on the filters was removed by heating to 90° C. in a solution of 10 mM Tris pH 7.5, 1 mM EDTA. The filterbound colony DNA's were rehybridized to 32p PM43-53. A single group 2 recombinant, PURUP88 was obtained (FIG. 6). Thus this invention provides a method for cloning wild type Gluconobacter DNA essential for production of L-sorbose dehydrogenase.

EXAMPLE 3

Transfer of Recombinant plasmids Containing L-Sorbose Dehydrogenase Related DNA to non 2KGA producing Gluconobacteria.

The recombinant plasmids were transferred to IFO 3293, a Gluconobacter which makes 0–2 g/l 2-KGA from 70 g/l of L-sorbose, and which is known to have L-sorbosone dehydrogenase activity. A spontaneous Nalidixic acid resistant (Nar) derivative of IF03293 was isolated by plating 50 μl of a stationary MB broth culture ona plate of MB agar, 100 μg/ml Na and picking a single colony. Recombinant plasmid transfer was carried out by tri-parental mating, utilizing E. coli J53 (RP4) as the helper strain. About 200 μl of stationary phase culturs of the recipient IFO 3293 grown in FB media (25 g/l fructose, 5 g/l yeast extract, 5 g/l bactopeptone), was mixed with about-100 μl each of the donor E. coli C600 (PURUH80, PURU010, or PURUH88) and the helper E. coli J53 (RP4) grown in LB media to mid log phase. About 75 μl of the mixture was plated on an 87 mm diameter nitrocellulose filter on the surface of a plate of FB agar (FB, 15 g/l agar). After about 16 hours at 30° C., the mixed colonies were streaked onto FB agar containing 10 μg/l polymixin B, 50 μg/ml Na, and 100 μg/ml streptomycin and further incubated at 30° C. 4–6 days. Only Gluconobacter IF03293 colonies which had received the desired recombinant plasmids were obtained this way. These cultures were grown in FB media at 30° C. 4 days, then 2 ml of this seed culture was transferred to 100 ml M3B media containing 100 μg/ml strep, and cultured at 30° C. with continuous agitation 5–7 days. Assays for 2-KGA were carried out (Table VI).

TABLE VI

Production of 2KGA by Recombinant Bacteria

| Host | Plasmid | 2KGA (g/L) |
|---|---|---|
| *E. coli* C600 | — | 0 |
| | RSF1010 | 0 |
| | PURUH80 | 0 |
| | PURUO10 | 0 |
| | PURUP88 | 0 |
| Gluconobacter IF03293 | — | 1.8 |
| | RSF1010 | 0.5 |
| | PURUH80 | 25 |
| | PURUO10 | 28 |
| | PURUP88 | 11.8 |

It is clear that the L-sorbose dehydrogenase gene related recombinant plasmids have complemented the 2-KGA deficiency of IFO3293. To confirm this, enzyme assays were performed on the recombinant cultures, as above. As seen from the results in Table VII, the recombinant Gluconobacteria were found to have L-sorbose dehydrogenase activities at least comparable to that of strain UV10, and considerably higher than that of the parent strain, IFO 3293.

TABLE VII

L-Sorbose Dehydrogenase Activity of Recombinant Gluconobacters

| | |
|---|---|
| UV10 | 0.194 U/mg |
| IF03293 | 0.019 |
| IF03293 (pURO10) | 0.2 |
| IF03293 (pURP88) | 0.13 |

We claim:

[1. A gluconobacter transformed with Tn5 which inactivates the 2-keto-L-Gulonic acid reductase and further having a recombinant plasmid which plasmid contains the DNA sequence effecting expression of L-sorbose dehydrogenase so that L-sorbose is converted to 2-KGA.]

[2. A gluconobacter transformed with Tn5 which inactivates the 2-keto-L-Gulonic acid reductase and which naturally produces L-sorbosone dehydrogenase but not L-sorbose dehydrogenase.]

[3. The Gluconobacter of claim 1 wherein said recombinant plasmid is a plasmid RSF1010 modified to contain DNA encoding L-sorbose dehydrogenase.]

*4. A transformed gluconobacter which has been obtained from a gluconobacter which produces L-sorbosone dehydrogenase but not L-sorbose dehydrogenase wherein said transformed gluconobacter:*

*1) had been transformed with Tn5 which inactivates the 2-keto-L-gulonic acid reductase, and*

*2) has a recombinant plasmid which plasmid has been modified to contain a DNA sequence from the L-sorbose dehydrogenase gene region of Gluconobacter oxydans UV10 (Accession Number FERM BP-1267) wherein said DNA sequence is selected from the group consisting of pUR H80, pUR 010, and uPR P88;* so that L-*sorbose is converted to 2-keto-L-gulonic acid.*

*5. The gluconobacter of claim 4 wherein said recombinant plasmid is plasmid RSF1010 modified to contain said DNA sequence.*

* * * * *